United States Patent [19]

Lewis et al.

[11] Patent Number: 5,184,501
[45] Date of Patent: Feb. 9, 1993

[54] EXHAUST SAMPLER AND CONTROL MEANS

[75] Inventors: Gary W. Lewis, Fountain Valley; Max J. Moore, Walnut, both of Calif.

[73] Assignee: Horiba Instruments Incorporated, Irvine, Calif.

[21] Appl. No.: 695,606

[22] Filed: May 3, 1991

[51] Int. Cl.⁵ .............................................. G01N 1/22
[52] U.S. Cl. .................................. 73/23.31; 73/863.01
[58] Field of Search ............ 73/23.31, 863.01, 863.02, 73/863.03

[56] References Cited

U.S. PATENT DOCUMENTS

| | | | |
|---|---|---|---|
| 3,593,023 | 7/1971 | Dodson et al. | 73/23.31 X |
| 3,603,155 | 9/1971 | Morris et al. | 73/23.31 X |
| 3,699,814 | 10/1972 | Kaufman . | |
| 3,817,100 | 6/1974 | Anderson et al. . | |
| 3,965,749 | 6/1976 | Hadden et al. | 73/23.31 |
| 4,586,367 | 5/1986 | Lewis . | |
| 4,660,408 | 4/1987 | Lewis . | |
| 4,823,591 | 4/1989 | Lewis | 73/3 |

Primary Examiner—Hezron E. Williams
Assistant Examiner—Joseph W. Roskos
Attorney, Agent, or Firm—Harness, Dickey & Pierce

[57] ABSTRACT

An exhaust sampler for use in evaluating exhaust emissions of an exhaust source such as an internal combustion engine which utilizes a calibrated subsonic venturi for measuring the exhaust or exhaust/dilution air flow rate. Controls are provided for selecting and controlling a variety of flow rates between or during test periods. The system also provides a variety of control methods for extracting a sample from the bulkstream flow of exhaust and dilution air or from raw exhaust flow.

32 Claims, 5 Drawing Sheets

EXHAUST SAMPLER AND CONTROL MEANS

BACKGROUND OF THE INVENTION

This invention relates to an improved exhaust sampler and control means, and more particularly to an apparatus for measuring the gaseous constituents of exhaust utilizing means for measuring the exhaust or exhaust/air mixture flow including a calibrated subsonic venturi, and means for controlling the flow rate of dilution air or exhaust/air mixture.

Under present day federal regulations, the exhaust emissions from motor vehicles must not exceed specified values of certain constituent contaminants, as set forth in the Code of Federal Regulations. See Title 40 of the Code of Federal Regulations, Parts 81-99, Subparts A, B, D, E, F, G, K and N. See also Kaufman U.S. Pat. No. 3,699,814. The presence of such standards has made it imperative that the exhaust emissions from vehicle engines be tested and analyzed to determine the relative amount of certain constituents therein. Much effort has gone into the development of equipment for use in this field of exhaust gas sampling, and it is now known to deliver exhaust gases from an internal combustion engine at an accurately controlled flow rate through a test apparatus for purposes of determining and analyzing the relative amounts of constituents therein. The general scheme of such testing is to add dilution air to the exhaust gases. The total volume of the mixture of exhaust and dilution air must be measured. A continuously proportional sample of volume must be collected and is stored for subsequent analysis of constituents such as hydrocarbons, carbon monoxide, and $NO_x$. Mass emissions are determined from the sample concentrations and total flow over the test period.

One such system for analyzing samples from exhaust gases is set forth in U.S. Pat. No. 3,699,814 to Kaufman entitled, "Gas Sampler," issued Oct. 24, 1972. The Kaufman patent, the disclosure of which is incorporated herein by reference, taught a much improved gaseous exhaust emission sampler which replaced the constant displacement pump of prior systems with a critical flow venturi and centrifugal blower for metering the diluted exhaust emissions at a constant volume flow.

Another system utilizes a pair of critical flow venturis for proportional sampling. An example of such a system is set forth in U.S. Pat. No. 3,817,100. In another such system, a downstream pump produces a sufficient vacuum on the bulkstream critical flow venturi exit so that the bulkstream mixture is flowing at sonic velocity, a condition which limits the bulkstream mixture to a constant mass flow rate at a given set of upstream temperature and pressure conditions measured at the bulkstream critical flow venturi inlet. A sample is extracted from the dilute bulkstream flow through another critical flow venturi in close proximity to the bulkstream critical flow venturi so that the venturis are operating under the same inlet pressure and temperature conditions. This sample critical flow venturi operates in connection with a downstream pump in the sampling line to create sonic flow, and thereby a constant mass flow rate at the measured upstream temperature and pressure conditions. Thus, the sample critical flow venturi extracts a sample for analysis at a flow rate proportional to the bulkstream flow rate.

Although the flow rate controlled by a critical flow venturi will vary a small amount due to changes in the venturi inlet temperature and pressure, if the sample venturi and bulkstream venturi are operating at critical flow rate conditions at identical inlet pressure and temperature conditions, the sample flow rate is extracted in proportion to the bulkstream flow rate.

Although this proportional sampling system using two critical flow venturis has certain advantages, it has a disadvantage in that it does not provide for active control of the bulkstream or sample flow rates to allow static and dynamic sampling of the bulkstream mixture. Consequently, such prior art systems cannot readily accommodate the testing of different sized internal combustion engines which generate substantially different exhaust flow volumes without using different bulkstream critical flow venturis.

It is, therefore, a principal object of this invention to provide an apparatus for sampling the emission content of exhaust from an exhaust source wherein a wide variety of flow rates may be selected and controlled between or during the test phases.

It is another object of this invention to provide an apparatus for sampling the emission content of exhaust from an exhaust source wherein the apparatus has a constant flow rate operating mode and a variable flow rate operating mode that provides a means for maintaining a constant dilution ratio with changing bulkstream or exhaust flow rate.

SUMMARY OF THE INVENTION

This invention is adapted to be embodied in an apparatus for sampling the emission content of exhaust from an exhaust source comprising an exhaust inlet adapted for connection with the exhaust source and an air inlet adapted for connection with the exhaust inlet to provide a mixture of exhaust and dilution air. The apparatus further includes means for defining a flow confining path for the mixture which has coupled within it means for establishing a flow of the mixture in the flow confining path. In accordance with the invention, there is provided means for measuring the flow rate of the mixture which comprises a subsonic venturi restriction, means for measuring at least one condition of the mixture upstream of the subsonic venturi, preferably the pressure and temperature of the mixture upstream of the subsonic venturi, means for measuring a condition, preferably the pressure, of the mixture in the throat of the subsonic venturi and a control unit for computing the flow rate of the mixture based on signals received from the upstream measuring means and from the subsonic venturi measuring means. In accordance with the invention, the sampling apparatus further comprises means for controlling the flow rate of the mixture in response to the computed flow rate of the mixture, means for extracting a sample of the mixture and means for controlling the flow rate of the extracted sample.

In another embodiment of the invention, an apparatus for sampling the emission content of exhaust from an exhaust source is provided which comprises an exhaust inlet adapted for connection with the exhaust source, means for defining a flow confining path for the exhaust and means coupled with the exhaust flow confining path for establishing a flow in the exhaust flow confining path. In accordance with the invention, there is provided means for measuring the flow rate of the exhaust comprising a subsonic venturi restriction, means for measuring at least one condition, preferably both pressure and temperature, of the exhaust upstream of the subsonic venturi, means for measuring a condition such as pressure of the exhaust in the subsonic venturi and a control unit for computing the flow rate of the exhaust based on signals received from the upstream and subsonic venturi measuring means. The apparatus further includes means for controlling the flow rate of the exhaust in response to the computed flow rate of the exhaust and means for extracting a sample of the exhaust which comprises a sample flow confining path. Means coupled to the sample flow confining path is provided for supplying dilution gas to the sample to provide a mixture of exhaust sample and dilution gas. In addition, the invention includes means for controlling the flow rate of the dilution gas in response to signals received from the control unit and means for controlling the flow rate of the mixture in response to signals received from the control unit.

In a further embodiment of the invention, there is provided an apparatus for sampling the emission content of exhaust from an exhaust source comprising an exhaust inlet adapted for connection with the exhaust source, means for defining a flow confining path for the exhaust, and means coupled with the exhaust flow confining path for establishing a flow therein. Means are provided for measuring the flow rate of the exhaust comprising a subsonic venturi restriction, means for measuring at least one condition, preferably both pressure and temperature, of the exhaust upstream of the subsonic venturi, means for measuring a condition such as pressure of the exhaust in the subsonic venturi and a control unit for computing the flow rate of the exhaust based on signals received from the upstream and subsonic venturi measuring means. Means for controlling the flow rate of the exhaust in response to the computed flow rate of the exhaust are also included. The sampling apparatus further comprises means for extracting a sample of the exhaust which includes a sample flow confining path. In accordance with the invention, means are provided for controlling the sample flow rate in response to signals received from the control unit. In addition, there are means coupled to the sample flow confining path downstream of the sample controlling means for supplying dilution gas to the sample to provide a mixture of exhaust sample and dilution gas, and means for controlling the flow rate of the dilution gas in response to signals received from the control unit.

DESCRIPTION OF THE PREFERRED
EMBODIMENTS OF THE INVENTION

Figure 1:
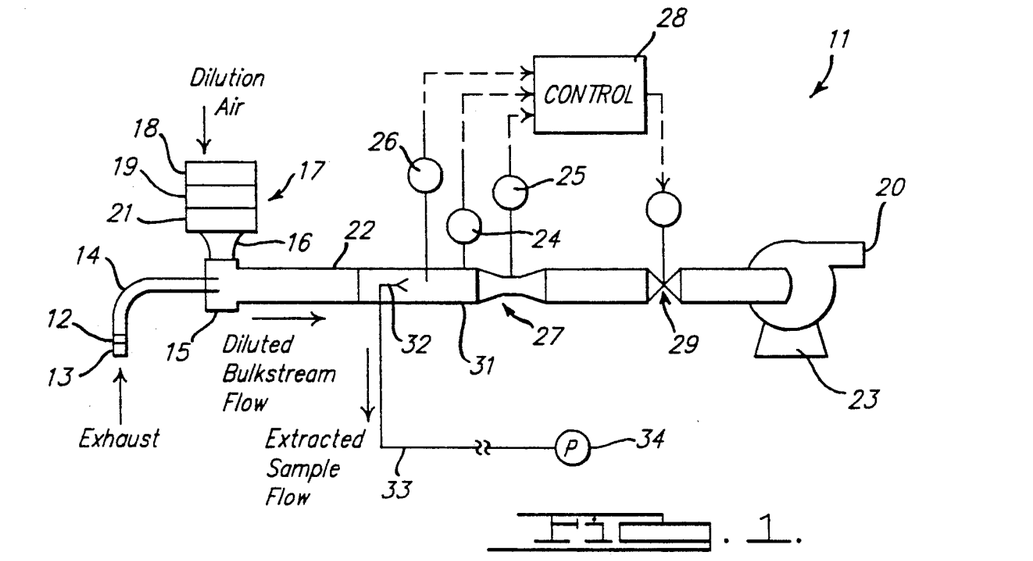
FIG. 1 is a diagrammatic illustration of an exhaust sampling system constructed in accordance with embodiments of the invention.

Referring first to FIG. 1, an apparatus for sampling and measuring the emission content of exhaust from a source is depicted and is identified generally by the reference numeral 11. The apparatus 11 comprises a tail pipe adapter 12 for coupling to an internal combustion engine exhaust tail pipe 13. Exhaust from the tail pipe 13 is introduced through an exhaust inlet pipe 14 into a mixing duct 15 which is coupled to an air stack 16 that receives ambient inlet air through a filter 17. This filter 17 may be implemented using a series of stacked filters such as a pre-filter 18, a charcoal filter 19 and an absolute filter 21. Filter assembly 17 serves generally to provide a supply of relatively pollution free inlet air which is mixed in the mixing duct 15 with the exhaust from the internal combustion engine or other exhaust source coupled to the exhaust inlet pipe 14.

The mixing duct 15 is coupled in a primary fluid defining path or line, designated generally by the reference numeral 22, through which the exhaust/inlet dilution air mixture flows. A single speed compressor unit or pump 23 is coupled in the primary fluid path 22 and provides vacuum pressure to establish the flow of the mixture, sometimes referred to as the bulkstream flow, in the primary fluid path 22. The flow establishing compressor unit or pump 23 vents to the atmosphere through a discharge vent 20.

In accordance with the invention, the bulkstream flow rate measurement is obtained using a pair of pressure transducers 24 and 25 and a temperature transducer 26 in connection with a calibrated subsonic venturi restriction 27. With a subsonic venturi restriction 27, if the upstream pressure and temperature of the mixture as well as the pressure at the throat of the subsonic venturi 27 are known, the bulkstream flow rate may then be computed. Thus, pressure and temperature transducers 24 and 26 are provided upstream of the subsonic venturi restriction 27 in a sampling zone 31 of the primary fluid path 22 for measuring the temperature and pressure respectively of the mixture immediately prior to entering the subsonic venturi 27. In addition, pressure transducer 25 is provided for measuring the subsonic venturi throat pressure of the mixture. These transducers 24, 26 and 25 are each electrically connected to a control unit 28 which may be a digital or analog computer and are each adapted to transmit electrical signals to the control unit 28 indicative of the sampling zone 31 pressure and temperature and throat pressure respectively. The control unit 28 computes the bulkstream flow rate based on the signals received from these pressure and temperature transducers 24, 25 and 26. The flow rates referred to herein with respect to the present invention are mass flow rates.

In accordance with the invention, there is provided downstream of the subsonic venturi 27 means for controlling the bulkstream flow rate. In the first embodiment, this controlling means comprises an adjustable flow control valve 29. As shown in FIG. 1, the flow control valve 29 is electrically connected to the control unit 28 so that it is adjusted automatically in response to the computed flow rate. However, it is possible to arrange the system so that the valve 29 is manually adjusted based on the computed flow rate.

As a method of control, the control unit 28 sends an electrical signal to the flow control valve 29 to adjust the bulkstream flow to create upstream pressure and temperature conditions, as measured by pressure and temperature transducers 24 and 26 respectively, which are substantially equal to the predetermined upstream pressure and temperature conditions which would exist under critical flow conditions. This creates critical flow pressure and temperature conditions in the sampling zone 31.

Thus, when a sample of the bulkstream flow is extracted from the sampling zone 31 by a critical flow venturi 32 which is operating under critical flow conditions in the sampling zone 31, the extracted sample flow rate through a sample flow path 33 will be proportional to the bulkstream flow rate, since the inlet pressure and temperature conditions of the extracted sample flow are simultaneously equal to the inlet pressure and temperature conditions of the controlled bulkstream flow. The sample critical flow venturi 32 meters the extracted sample flow and is used to control and stabilize the extracted sample flow in the sample line 33, independent of the downstream vacuum, by virtue of sonic flow at the throat of the venturi 32. A pump 34 is positioned downstream of the critical flow venturi 32 to provide a sufficient vacuum at the exit of the venturi 32 to maintain sonic or critical flow.

Although the flow rate controlled by a critical flow venturi will vary a small amount due to changes in venturi inlet pressure and temperature, if both a sample and a bulkstream critical flow venturi are used and are arranged so that they have identical inlet critical flow rate temperature and pressure conditions, the upstream inlet temperature and pressure variations will affect each in the same manner so that the sample flow rate will be extracted proportional to the bulkstream flow rate. Thus, the sampling apparatus of the first embodiment allows for active control of the bulkstream flow rate to simulate the flow control of a critical flow venturi, thus allowing the use of the sample critical flow venturi 32 for proportional sampling.

In a second embodiment, the control valve 29 may be eliminated if a variable speed compressor, turbocompressor, or variable speed positive displacement pump is used as the flow establishing means in place of the single speed compressor or pump 23. In this case, the variable speed pump, compressor or turbocompressor preferably will be electrically connected to the control unit 28 so that the variable speed pump, compressor or turbocompressor is automatically adjusted in response to the computed flow rate. This arrangement is applicable to all embodiments.

FIGS. 2 through 8 diagrammatically illustrate alternative apparatuses for sampling the emission content of exhaust from an exhaust source which are constructed in accordance with additional embodiments of the invention. The apparatuses of each of these additional embodiments are generally similar to that described in connection with the first embodiment. For that reason, components of these additional embodiments which are the same as components of the first embodiment are identified by the same reference numerals and will not be described again, except insofar as is necessary to understand the construction and operation of these additional embodiments.

Figure 2:
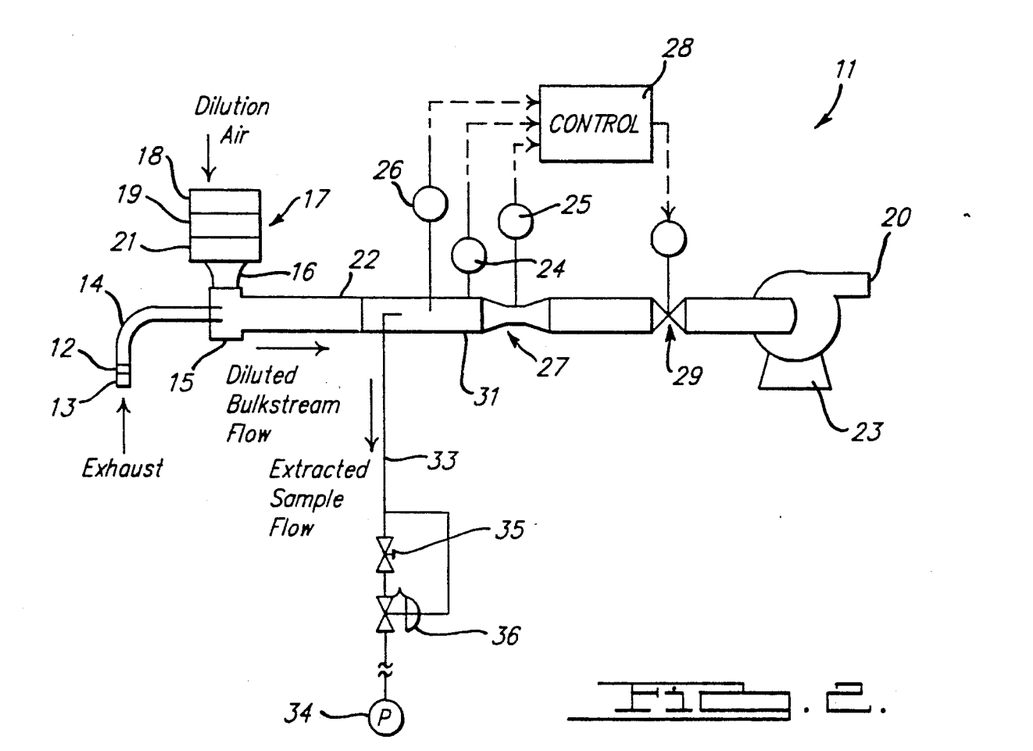
FIG. 2 is a diagrammatic illustration of an exhaust sampling system showing a third embodiment of the invention.

FIG. 2 shows a third embodiment of the invention in which the sample critical flow venturi 32 is replaced by a sampling duct coupled to the sample line 33 in the sampling zone 31. An adjustable flow control valve 35 and differential pressure regulator 36 are used to regulate or meter the extracted sample flow through sample line 33 at a desired constant flow rate. The flow control valve 35, which is used to select a desired flow rate for the extracted sample, establishes a pressure differential between its inlet side and its outlet side. After an extracted sample flow rate is selected, it is held constant by the differential pressure regulator 36 that is coupled with sample fluid path 33 to receive extracted sample flow both upstream and downstream of the flow control valve 35. The differential pressure regulator 36 determines the pressure differential between this upstream and downstream flow with respect to the control valve 35 to maintain the pre-selected constant mass flow rate for the extracted sample. The bulkstream flow rate is controlled by the subsonic venturi restriction 27 and flow control valve 29 to maintain a constant ratio of the extracted sample flow rate to the bulkstream flow rate during the testing period. Thus, the sample flow rate is proportional to the bulkstream flow rate, allowing for proportional sampling.

Figure 3:
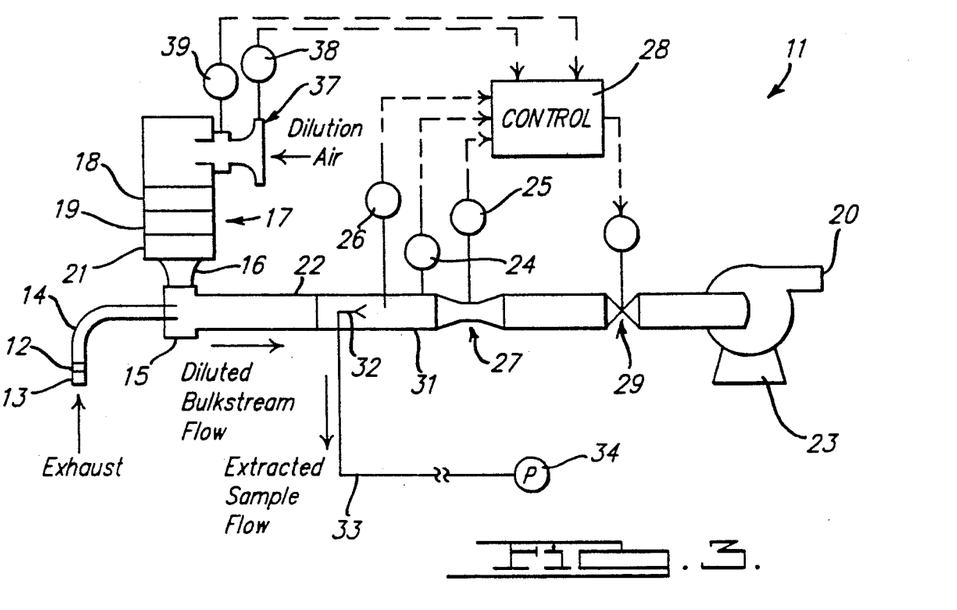
FIG. 3 is a diagrammatic illustration of an exhaust sampling system showing a fourth embodiment of the invention.

Referring now to FIG. 3, a fourth embodiment of an exhaust sampling apparatus is depicted wherein the exhaust flow rate may be directly determined, and the sample is extracted using the critical flow venturi 32. The apparatus of this fourth embodiment contains all of the components of that of the first embodiment, and in addition includes a calibrated subsonic venturi restriction 37 for the dilution air. This subsonic venturi 37 is coupled to the air stack 16 as shown in FIG. 3 and acts to meter the inlet dilution air flow rate. To determine the dilution air flow rate using this venturi 37, the external dilution air temperature is measured by a temperature transducer 38 and the dilution air pressure is measured at the throat of the venturi 37 by a pressure transducer 39. These transducers 38 and 39 transmit their respective signals to the control unit 28 where they are processed. The bulkstream flow rate is computed as described in connection with the first embodiment and the exhaust flow rate is calculated as the bulkstream flow rate less the dilution air flow rate. Adjustable flow control valve 29 is used to adjust the bulkstream flow rate to maintain conditions simulating the performance of a critical flow venturi. In this case, the extracted sample flow rate through the critical flow venturi 32 may be determined by the pressure and temperature measurements taken by transducers 24 and 26 in sampling zone 31. The integrated bag sample volume analyzed concentration can then be corrected by control unit 28 to account for variations in the bulkstream flow rate during the test period to provide a correlation to the results that would be obtained using the critical flow venturi test equipment described in the aforementioned Kaufman patent.

Figure 4:
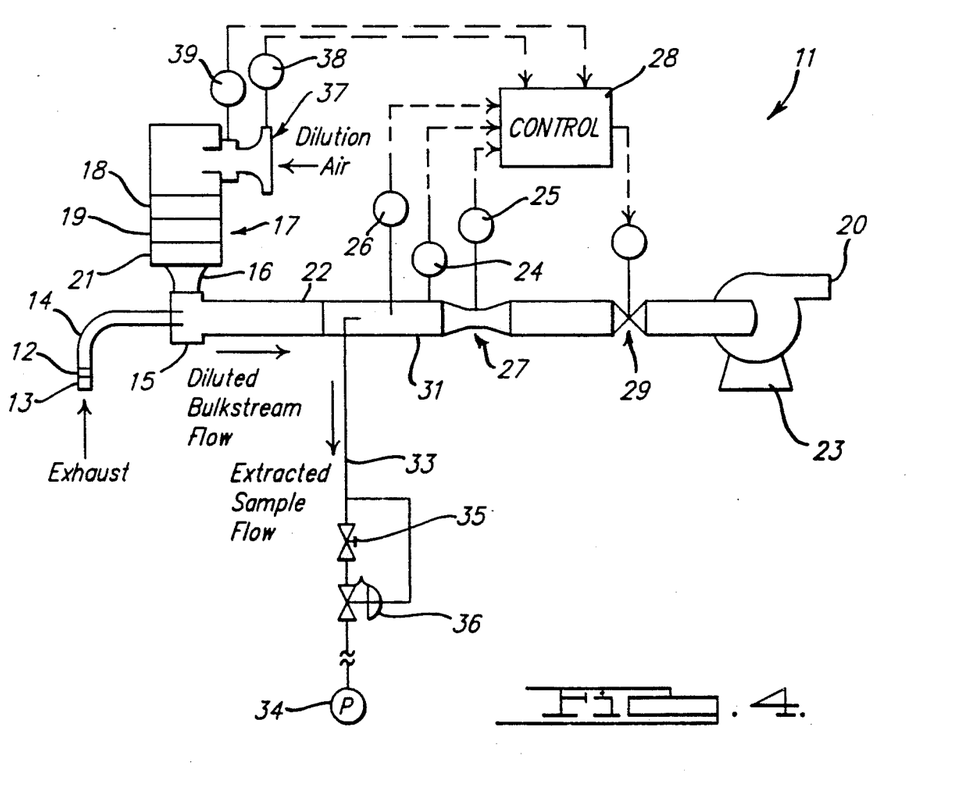
FIG. 4 is a diagrammatic illustration of an exhaust sampling system showing a fifth embodiment of the invention.

FIG. 4 diagrammatically shows a fifth embodiment of the sampling apparatus wherein a constant ratio of dilution air flow rate to exhaust flow rate is maintained and the sample is extracted at a fixed mass flow rate. This fifth embodiment utilizes the flow control valve 35 and differential pressure regulator 36 of the third embodiment to provide the fixed mass flow rate for the extracted sample, eliminating the critical flow venturi 32 and the need for pressure and temperature corrections with respect thereto. Thus, this fifth embodiment has the capability of easily selecting a fixed sample flow rate for special tests.

As shown in FIG. 4, this fifth embodiment also incorporates the dilution air flow rate measurement equipment of the fourth embodiment, as well as the control features of that embodiment to adjust the bulkstream flow rate to maintain a fixed ratio of dilution air to exhaust flow rates.

Figure 5:
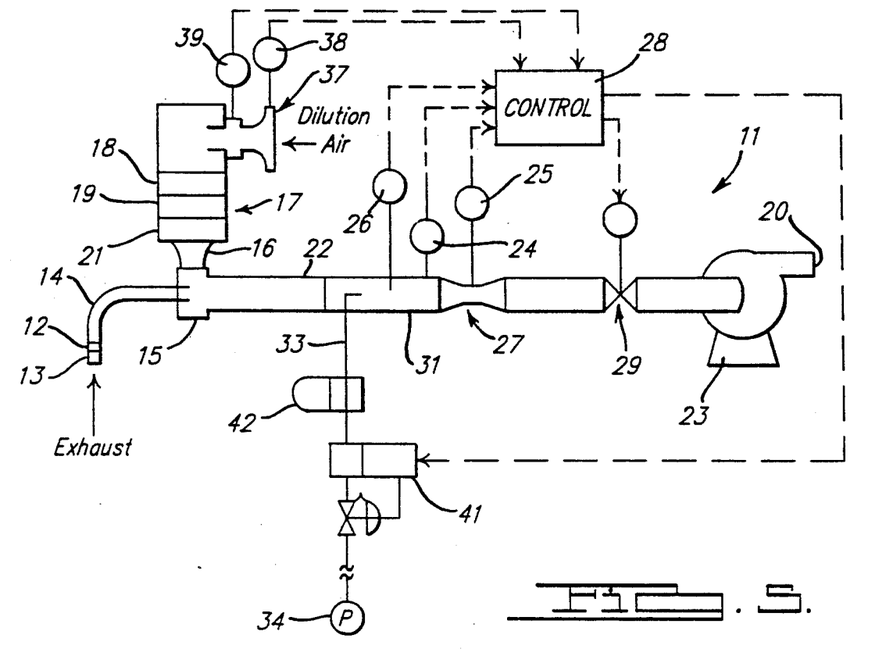
FIG. 5 is a diagrammatic illustration of an exhaust sampling system showing a sixth embodiment of the invention.

In a sixth embodiment illustrated in FIG. 5, a sampling apparatus is depicted which provides for active control of the ratio of dilution air to exhaust flow rates with proportional sample flow rate control. In this sixth embodiment, a mass flow meter 41 is positioned in the sample line 33 for measuring and controlling the mass flow rate therethrough and for receiving an electrical signal from the control unit 28 to provide sample flow rate adjustment. A filter 42 is located in the sample path 33 upstream of the mass flow meter 41 to remove particulates and prevent them from contaminating the flow meter 41.

Various control modes may be used with this embodiment. For example, the sample flow rate may be controlled by mass flow meter 41 so that it is proportional to the bulkstream flow rate as determined using the subsonic venturi 27. Alternatively, the sample flow rate may be controlled to simulate an integrated volume similar to the critical flow venturi equipment described in Kaufman. Another alternative is to maintain a preselected, constant sample flow rate.

Figure 6:
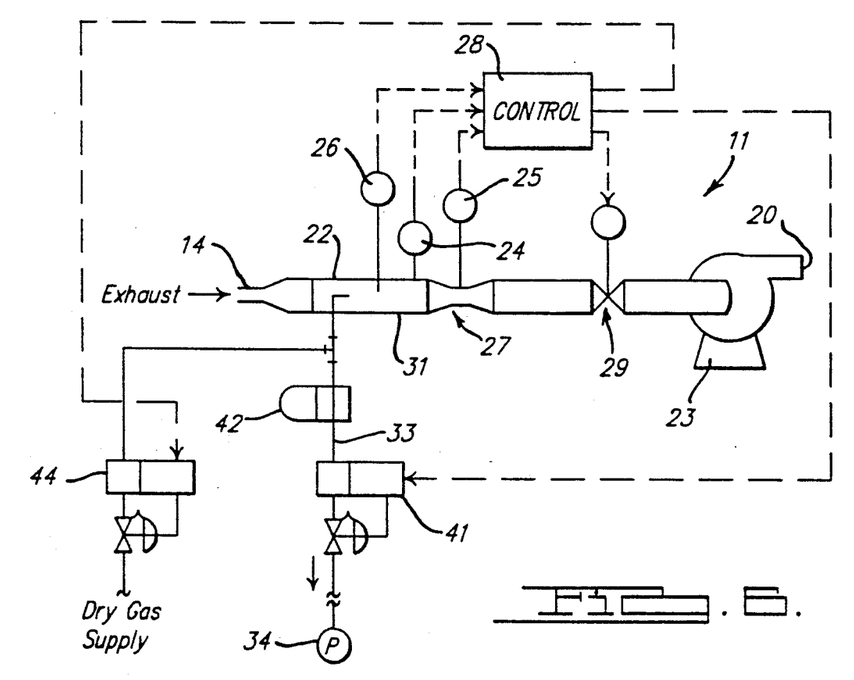
FIG. 6 is a diagrammatic illustration of an exhaust sampling system showing a seventh embodiment of the invention.

Referring now to FIG. 6, a seventh embodiment of the invention is illustrated which involves raw exhaust sample extraction with extracted sample dilution control. The air stack 16 and associated components are eliminated. In this embodiment, a dry gas supply line, identified by the reference numeral 43, is coupled to the sample line 33 upstream of the mass flow meter 41 and filter 42. Another mass flow meter 44 is coupled in the dry gas supply line 43 for regulating the mass flow rate of the dry gas which is used to dilute the extracted raw exhaust sample.

The diluted sample flow rate through sample line 33 is controlled by mass flow meter 41 as described with reference to FIG. 5. The dry gas mass flow meter 44 receives an electrical signal from the control unit 28 for active control of the dry gas flow rate. Flow control valve 29 is adjusted by the control unit 28 to maintain the pressure in the sampling zone 31, as measured by pressure transducer 24, at zero value so that the flow rate measured using the subsonic venturi 27 is the exhaust flow rate.

Active control of the dry gas flow rate by mass flow meter 44 and active control of the extracted diluted sample flow rate by mass flow meter 41 allows two methods of obtaining a proportional diluted sample. The first involves a fixed dilution ratio, wherein the extracted diluted sample flow rate and dry gas flow rate are controlled proportionately to the exhaust flow rate to maintain a constant dilution ratio of dry gas flow rate to exhaust flow rate.

In the second control method, which emulates the "classical" critical flow venturi equipment of Kaufman, the extracted diluted sample flow rate is set at a fixed value. The dry gas flow rate is adjusted by the control unit 28 so that the dry gas flow rate is inversely proportional to the exhaust flow rate, scaled with the extracted sample flow rate. Thus, if the exhaust flow rate equals zero, then the dry gas flow rate equals the extracted sample flow rate. If the exhaust flow rate is at the maximum value for the size of the engine tested, then the dry gas flow rate equals one-half of the extracted sample flow rate, resulting in a dilution ratio of dry gas flow rate to exhaust flow rate of 1:1.

Figure 7:
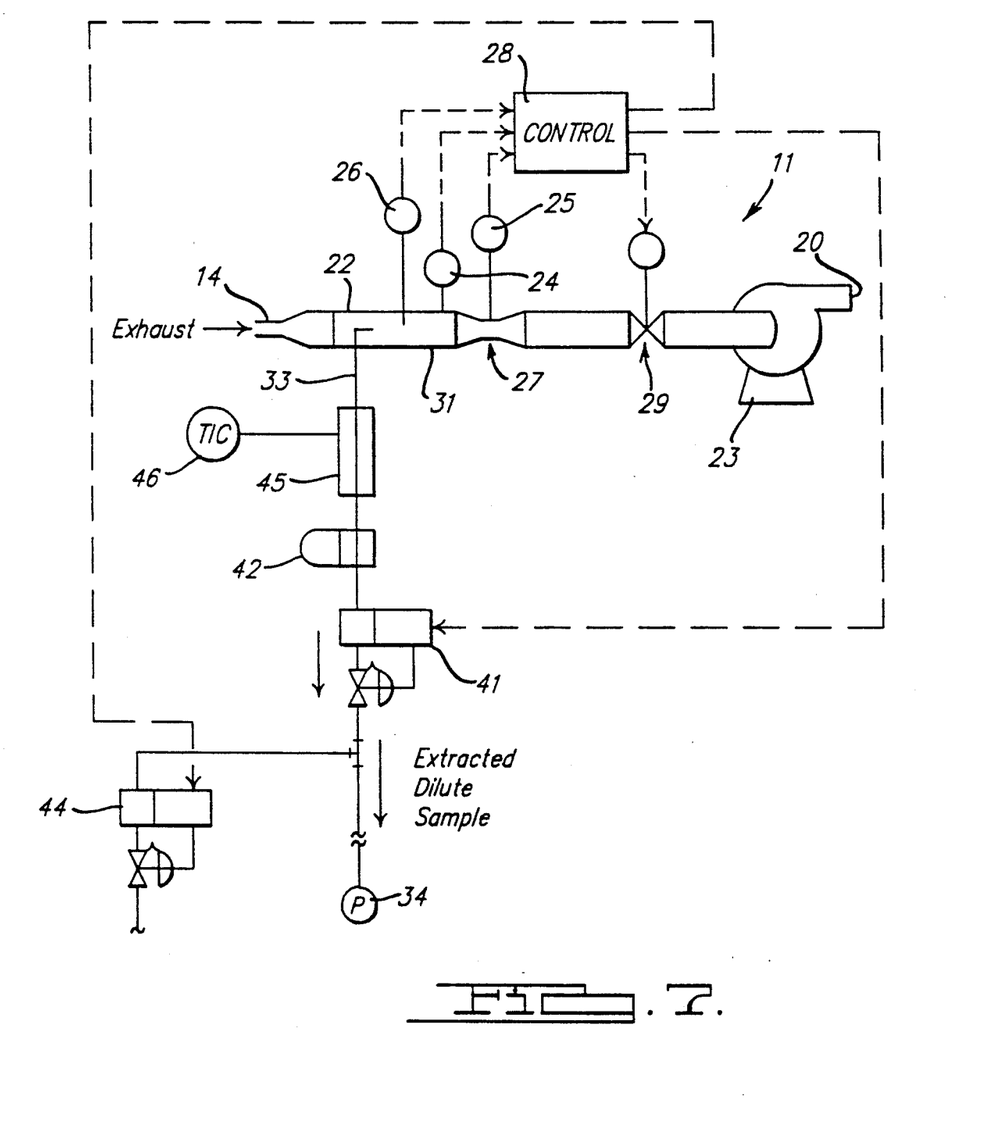
FIG. 7 is a diagrammatic illustration of an exhaust sampling system showing a eighth embodiment of the invention.

An eighth embodiment of the invention is shown in FIG. 7, which is generally similar to the seventh embodiment in that the air stack 16 and associated components are not used. In this embodiment, the sample line 33 may be heated by means of a heater 45 that encloses a portion of the line 33. Coupled to the heater 45 is a temperature regulator 46 for controlling the temperature of the heater 45. The dry gas supply line 43 is coupled to the sample line 33 downstream of the mass flow meter 41 which controls the sample flow rate. As in the seventh embodiment, the mass flow meter 44 regulates the dry gas flow rate.

In this eighth embodiment, a raw exhaust sample is extracted from the exhaust flow through the heated sample line 33 and is filtered by filter 42. The two methods for obtaining a proportional sample described in conjunction with the seventh embodiment may then be used. The sampling apparatus of the eighth embodiment may be used with or without the heater 45 and accompanying temperature controller 46.

Figure 8:
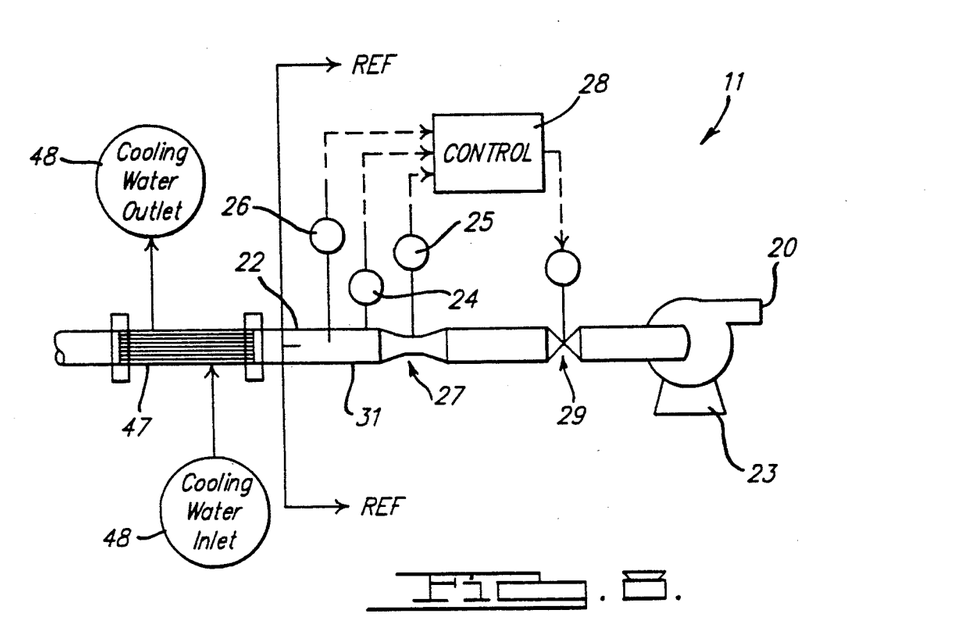
FIG. 8 is a diagrammatic illustration of an exhaust sampling system showing a sampling apparatus wherein a flow straightener or heat exchanger is positioned upstream of the subsonic venturi restriction. The flow straightener or heat exchanger are applicable to all embodiments of the invention.

Referring now to FIG. 8, a sampling apparatus which incorporates a flow straightener identified by the reference numeral 47 is coupled with the primary fluid line 22 upstream of the subsonic venturi 27. The flow straightener 47 usually consists of tubing bundled together and contained within a piece of pipe; fluid flows through the bundle of tubing. Alternatively, or in addition, the sampling apparatus may contain a heat exchanger 48 that has an inlet and an outlet so that cooling fluid may be circulated through the tubing to cool the bulkstream flow.

The flow straightener 47 may be used with all of the described embodiments but is particularly useful for the raw sampling embodiments shown in FIGS. 6 and 7. The flow straightener acts to minimize gas turbulence which may occur under certain operating conditions. Exhaust pulsations usually occur at engine idle settings, and the flow straightener 47 will minimize the pulsations before the flow reaches the subsonic venturi 27.

The heat exchanger 48 may be used in place of the flow straightener 47 and in addition to straightening the flow will also cool the bulkstream mixture or raw exhaust flow thus reducing the sample temperature changes. This, in turn, will reduce the amount of correction required by the control unit 28.

Figure 9:
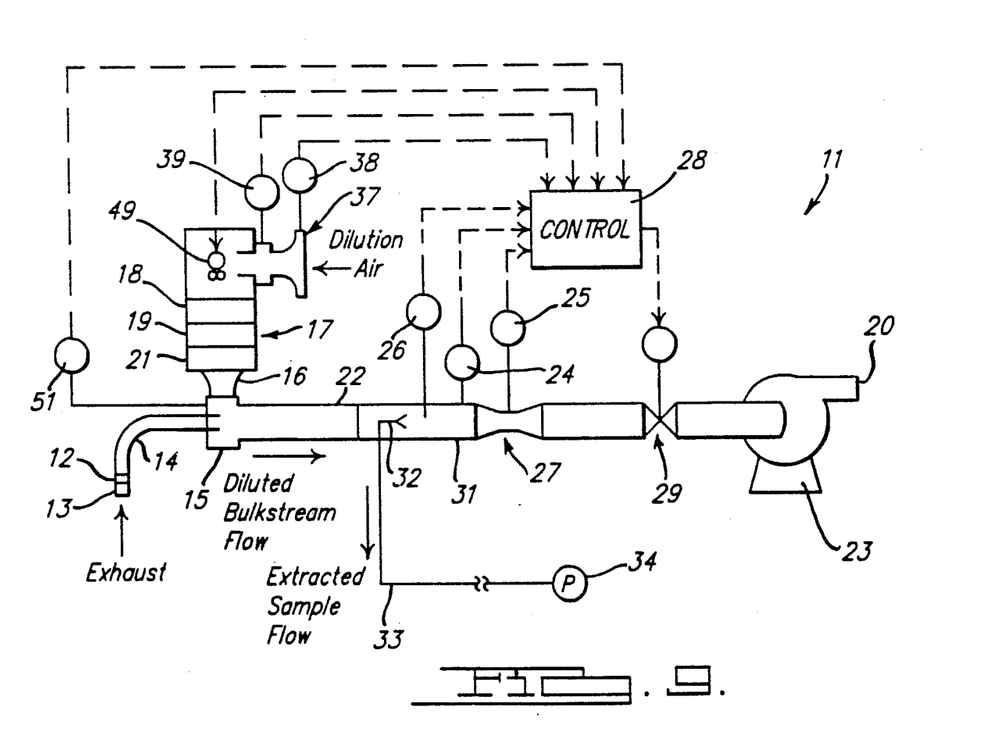
FIG. 9 is a diagrammatic illustration of an exhaust sampling system showing a sampling apparatus wherein a variable speed blower is positioned between the dilution air subsonic venturi and dilution air filter assembly. This arrangement can be used in connection with the third, fourth, fifth, sixth and seventh embodiments of the invention.

In FIG. 9, an exhaust sampling apparatus is shown which has a variable speed blower or fan 49 positioned between the dilution air subsonic venturi 37 and dilution air filter assembly 17. The blower 49 receives electrical signals from the control unit 28 which controls the blower or fan speed to control the dilution air flow rate. The blower or fan speed is controlled so that the pressure sensed by a pressure transducer 51 positioned in the mixing duct 15 is maintained at a preset value, usually zero atmospheric pressure, so that the pressure reflected at the vehicle tailpipe 14 sees no effect of the test equipment. Alternatively, the system can be arranged so that this control is based on pressure signals of transducer 24 in the sampling zone 31.

The blower speed may also be controlled, in conjunction with bulkstream flow rate, to obtain additional dilution ratios, unattainable with non force-fed dilution air.

It should be readily apparent from the foregoing description that various embodiments of a highly effective and versatile exhaust sampler for sampling the emission content of exhaust from an exhaust source has been illustrated and described. The control means associated with the exhaust sampler is able to select and control a variety of flow rates and to provide variety of control methods for extracting a sample from a bulkstream flow of exhaust and air or from a raw exhaust flow. Although various embodiments have been illustrated and described, it is to be understood that various changes and modifications may be made without departing from the spirit and scope of the invention, as defined by the appended claims.

We claim:

1. An apparatus for sampling the emission content of exhaust from an exhaust source comprising an exhaust inlet adapted for connection with the exhaust source, a dilution air inlet adapted for connection with said exhaust inlet to provide a mixture of exhaust and dilution air, means for defining a flow confining path for said mixture, means coupled with said flow confining path for establishing a flow of said mixture in said flow confining path, means for measuring the flow rate of said mixture comprising a subsonic venturi restriction, means for measuring the pressure and temperature of said mixture upstream of said subsonic venturi, means for measuring the pressure of said mixture in said subsonic venturi and a control unit for computing the flow rate of said mixture based on signals received from said upstream measuring means and said subsonic venturi measuring means, said sampling apparatus further comprising means for controlling the flow rate of said mixture in response to the computed flow rate of said mixture, means for extracting a sample of said mixture and means for controlling the flow rate of the extracted sample so as to maintain a preselected constant mass flow rate of said extracted sample.

2. An apparatus as recited in claim 1, wherein said sample extracting means comprises a sample flow confining path and means coupled with said sample flow confining path for establishing a sample flow and wherein said sample flow rate controlling means comprises a critical flow venturi restriction coupled to said sample flow confining path and positioned upstream of said subsonic venturi.

3. An apparatus as recited in claim 2, wherein said sample flow establishing means is operated to insure that said critical flow venturi operates under critical flow conditions and said mixture flow rate controlling means is controlled to insure that the temperature and pressure upstream of said subsonic venturi are maintained to emulate critical flow conditions upstream of said subsonic venturi for proportional sampling.

4. An apparatus as recited in claim 2, further comprising means for measuring the flow rate of the dilution air comprising a subsonic venturi restriction coupled to said air inlet, means for measuring the temperature of the dilution air upstream of said dilution air subsonic venturi and means for measuring the pressure of the dilution air in said dilution air subsonic venturi, the flow rate of said mixture being controlled so as to maintain conditions simulating the performance of a critical flow venturi.

5. An apparatus as recited in claim 2, further comprising means for measuring the flow rate of the dilution air comprising a subsonic venturi restriction coupled to said air inlet, means for measuring the temperature of the dilution air upstream of said dilution air subsonic venturi and means for measuring the pressure of the dilution air in said dilution air subsonic venturi, and means for controlling the flow rate of the dilution air comprising a blower positioned downstream of said dilution air subsonic venturi and a pressure transducer for measuring the pressure of the mixture, the flow rate of the dilution air being controlled so as to maintain a preset pressure as measured by said pressure transducer.

6. An apparatus as recited claim 2, further comprising means for measuring the flow rate of the dilution air comprising a subsonic venturi restriction coupled to said air inlet, means for measuring the temperature of the dilution air upstream of said dilution air subsonic venturi and means for measuring the pressure of the dilution air in said dilution air subsonic venturi, and means for controlling the flow rate of the dilution air comprising a blower positioned downstream of said dilution air subsonic venturi and a pressure transducer for measuring the pressure of the mixture, the flow rate of the dilution air and the flow rate of said mixture being controlled so as to maintain a fixed dilution ratio of dilution air flow rate to exhaust flow rate and a preset pressure as measured by said pressure transducer.

7. An apparatus as recited in claim 1, wherein said sample extracting means comprises a sample flow confining path and means coupled with said sample flow confining path for establishing a sample flow and wherein said sample flow ate controlling means comprises adjustable valve means and means for measuring the pressure of the sample flow upstream and downstream of said adjustable valve means for controlling the sample flow rate.

8. An apparatus as recited in claim 7, wherein the ratio of the mixture flow rate to the sample flow rate is held constant for proportional sampling.

9. An apparatus as recited in claim 7, further comprising means for measuring the flow rate of the dilution air comprising a subsonic venturi restriction coupled to said air inlet, means for measuring the temperature of the dilution air upstream of said dilution air subsonic venturi and means for measuring the pressure of the dilution air in said dilution air subsonic venturi, the flow rate of said mixture being controlled so as to maintain a fixed ratio of the dilution air flow rate to exhaust flow rate.

10. An apparatus as recited in claim 1, wherein said mixture flow establishing means comprises a fixed flow rate pump.

11. An apparatus as recited in claim 10, wherein said mixture controlling means comprises an adjustable valve positioned downstream of said subsonic venturi and upstream of said fixed flow rate pump.

12. An apparatus as recited in claim 1, wherein said mixture flow establishing means and said mixture flow rate controlling means comprises a variable speed compressor.

13. An apparatus as recited in claim 1, wherein said mixture flow establishing means and said mixture flow rate controlling means comprises a variable speed positive displacement pump.

14. An apparatus as recited in claim 1, further comprising means for measuring the flow rate of the dilution air comprising a subsonic venturi restriction coupled to said air inlet, means for measuring the temperature of the dilution air upstream of said dilution air subsonic venturi and means for measuring the pressure of the dilution air in said dilution air subsonic venturi, and wherein said sample extracting means comprises a sample flow confining path and means coupled with said sample flow confining path for establishing a sample flow, said sample flow rate controlling means comprising a mass flow controller controlled by said control unit so that the sample flow rate is proportional to said mixture flow rate.

15. An apparatus for sampling the emission content of exhaust from an exhaust source comprising an exhaust inlet adapted for connection with the exhaust source, means for defining a flow confining path for said exhaust, means coupled with said exhaust flow confining path for establishing a flow in said exhaust flow confining path, means for measuring the flow rate of said exhaust comprising a subsonic venturi restriction, means for measuring the pressure and temperature of said exhaust upstream of said subsonic venturi, means for measuring the pressure of said exhaust in said subsonic venturi and a control unit for computing the flow rate of said exhaust based on signals received from said upstream measuring means and said subsonic venturi measuring means, and means for controlling the flow rate of said exhaust in response to the computed flow rate of said exhaust, said sampling apparatus further comprising means for extracting a sample of said exhaust comprising a sample flow confining path, means coupled to said sample flow confining path for supplying dilution gas to said sample to provide a mixture of exhaust sample and dilution gas, means for controlling the flow rate of the dilution gas in response to signals received from said control unit and means for controlling the flow rate of said mixture in response to signals received from said control unit so as to maintain a preselected constant mass flow rate of said mixture of exhaust sample and dilution gas.

16. An apparatus as recited in claim 15, wherein the extracted sample mixture flow rate and dilution gas flow rate are controlled proportional to the exhaust flow rate to maintain a constant dilution ratio of dilution gas flow rate to exhaust flow rate.

17. An apparatus as recited in claim 15, wherein the extracted sample mixture flow rate is set at a constant value and wherein the dilution gas flow rate is controlled so that it is inversely proportional to the exhaust flow rate, scaled with the extracted sample mixture flow rate.

18. An apparatus as recited in claim 15, wherein said flow confining path means comprises a flow straightener upstream of said subsonic venturi.

19. An apparatus as recited in claim 15, wherein said flow confining path means comprises a heat exchanger upstream of said subsonic venturi.

20. An apparatus for sampling the emission content of exhaust from an exhaust source comprising an exhaust inlet adapted for connection with the exhaust source, means for defining a flow confining path for said exhaust, means coupled with said exhaust flow confining path for establishing a flow in said exhaust flow confining path, means for measuring the flow rate of said exhaust comprising a subsonic venturi restriction, means for measuring the pressure and temperature of said exhaust upstream of said subsonic venturi, means for measuring the pressure of said exhaust in said subsonic venturi and a control unit for computing the flow rate of said exhaust based on signal received from said upstream measuring means and said subsonic venturi measuring means and means for controlling the flow rate of said exhaust in response to the computed flow rate of said exhaust, said sampling apparatus further comprising means for extracting a sample of said exhaust comprising a sample flow confining path, means for controlling the flow rate of said sample in response to signals received from said control unit so as to maintain a preselected constant mass flow rate of said sample, means coupled to said sample flow confining path downstream of said sample controlling means for supplying dilution gas to said sample to provide a mixture of exhaust sample and dilution gas, and means for controlling the flow rate of the dilution gas in response to signals received from said control unit.

21. An apparatus as recited in claim 20, wherein the extracted sample flow rate and dilution gas flow rate are controlled proportional to the exhaust flow rate to maintain a constant dilution ratio of dilution gas flow rate to exhaust gas flow rate.

22. An apparatus as recited in claim 20, wherein the extracted sample flow rate is set at a constant value and wherein the dilution gas flow rate is controlled so that it is inversely proportional to the exhaust flow rate, scaled with the extracted sample flow rate.

23. An apparatus as recited in claim 20, wherein said flow confining path means comprises a heat exchanger upstream of said subsonic venturi.

24. An apparatus as recited in claim 20, wherein said flow confining path means comprises a heat exchanger upstream of said subsonic venturi.

25. An apparatus for sampling the emission content of exhaust from an exhaust source comprising:
an exhaust inlet adapted for connection with the exhaust source;
a dilution air inlet adapted for connection with said exhaust inlet to provide a mixture of exhaust and dilution air;
means for defining flow confining path for said mixture;
flow control means coupled with said flow confining path for establishing a flow of said mixture in said flow confining path;
means for measuring the flow rate of said mixture including a subsonic venturi restriction;
sampling zone located in said flow confining path upstream of said subsonic venturi restriction;
means for extracting a sample of the mixture flowing through said sampling zone including means defining a sample flow path and for maintaining a preselected constant mass flow rate through said sample flow path; and
controller means responsive to said measuring means for controlling said flow control means so as to create a predetermined mass flow rate of said mixture through said sampling zone related to said preselected constant mass flow rate of said extracted sample.

26. The apparatus of claim 25 wherein said controller means is adapted to maintain a constant ratio between the mass flow rate of said mixture through said sampling zone and the preselected constant mass flow rate through said sample flow path.

27. The apparatus of claim 26 wherein said measuring means includes transducer means for producing signals proportional to a characteristic of said mixture upstream of said subsonic venturi restriction and a characteristic of said mixture in said subsonic venturi restriction.

28. The apparatus of claim 27 wherein said extracting means includes a critical flow venturi connected to said sampling zone and means for maintaining a mass flow rate through said critical flow venturi at the critical flow condition of said critical flow venturi.

29. The apparatus of claim 28 wherein said controller means is responsive to said signals from said measuring means for controlling said flow control means so as to create a predetermined mass flow rate of said mixture through said sampling zone related to said critical flow condition of said critical flow venturi.

30. The apparatus of claim 27 wherein said extracting means includes an adjustable flow control valve connected to said sampling zone and a differential pressure regulator connected to said adjustable flow control valve for maintaining constant the pressure differential across said adjustable flow control valve.

31. The apparatus of claim 27 wherein said extracting means includes a mass flow meter adapted to receive a control signal from said controller means for controlling the flow through said sample flow path.

32. An apparatus for sampling the emission content of exhaust from an exhaust source comprising:

an exhaust inlet adapted for connection with the exhaust source;

a dilution air inlet adapted for connection with said exhaust inlet to provide a mixture of exhaust and dilution air;

means for defining a flow confining path for said mixture;

flow control means coupled with said flow confining path for establishing a flow of said mixture in said flow confining path;

means fur measuring the flow rate of said mixture including a subsonic venturi restriction and transducer means for producing signals proportional to the temperature and pressure of said mixture upstream of said subsonic venturi restriction and the pressure of said mixture in said subsonic venturi restriction;

a sampling zone located in said flow confining path upstream of said subsonic venturi restriction;

means for extracting a sample of the mixture flowing through said flow confining path including a critical flow venturi connected to said sampling zone and means for maintaining a flow rate through said critical flow venturi at the critical flow condition of said critical flow venturi; and controller means responsive to said signals from said transducer means for controlling said flow control means so as to create predetermined pressure and temperature conditions in said sampling zone corresponding to said critical flow condition of said critical flow venturi.

* * * * *

UNITED STATES PATENT AND TRADEMARK OFFICE
CERTIFICATE OF CORRECTION

PATENT NO. : 5,184,501
DATED : February 9, 1993
INVENTOR(S) : Gary W. Lewis et al.

It is certified that error appears in the above-identified patent and that said Letters Patent is hereby corrected as shown below:

Column 10, line 20, claim 6,
  after "recited", insert --in--.

Column 10, line 39, claim 7,
  "ate" should be --rate--.

Column 12, line 8, claim 20,
  "signal" should be --signals--.

Column 12, line 35, claim 23,
  delete "heat exchanger" and insert --flow straightener--.

Column 14, line 11, claim 32,
  "fur" should be --for--.

Signed and Sealed this

Seventh Day of December, 1993

Attest:

BRUCE LEHMAN

*Attesting Officer*      *Commissioner of Patents and Trademarks*